United States Patent
Blakley

(10) Patent No.: US 7,117,743 B2
(45) Date of Patent: Oct. 10, 2006

(54) MULTIPLE-TRANSDUCER SENSOR SYSTEM AND METHOD WITH SELECTIVE ACTIVATION AND ISOLATION OF INDIVIDUAL TRANSDUCERS

(75) Inventor: Daniel R. Blakley, Philomath, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 23 days.

(21) Appl. No.: 10/632,290

(22) Filed: Jul. 31, 2003

(65) Prior Publication Data

US 2005/0022601 A1  Feb. 3, 2005

(51) Int. Cl.
*G01N 9/24* (2006.01)
(52) U.S. Cl. .................. 73/602; 73/24.06; 73/31.06
(58) Field of Classification Search .............. 73/602, 73/618, 620, 625, 626, 627, 628, 19.03, 24.06, 73/31.05, 31.06, 64.53, 61.79; 600/443, 600/447
See application file for complete search history.

(56) References Cited

U.S. PATENT DOCUMENTS

| | | | |
|---|---|---|---|
| 3,582,838 A | 6/1971 | DeVries | |
| 3,983,424 A | 9/1976 | Parks | |
| 4,055,072 A | 10/1977 | Fletcher et al. | |
| 4,253,338 A | 3/1981 | Iinuma et al. | |
| 4,305,158 A * | 12/1981 | Fujishima et al. | 455/187.1 |
| 4,332,171 A | 6/1982 | Iida et al. | |
| 4,448,076 A | 5/1984 | van Heelsbergen | |
| 4,766,554 A | 8/1988 | Sarr et al. | |
| 4,788,466 A | 11/1988 | Paul et al. | |
| 5,044,462 A * | 9/1991 | Maki, Jr. | 181/103 |
| 5,060,651 A * | 10/1991 | Kondo et al. | 600/443 |
| 5,119,342 A * | 6/1992 | Harrison et al. | 367/7 |
| 5,189,914 A * | 3/1993 | White et al. | 73/599 |
| 5,201,215 A | 4/1993 | Granstaff et al. | |
| 5,325,704 A * | 7/1994 | Mariani et al. | 73/24.06 |
| 5,448,126 A | 9/1995 | Eda et al. | |
| 5,477,098 A | 12/1995 | Eguchi et al. | |
| 5,488,866 A * | 2/1996 | Ravel et al. | 73/579 |

(Continued)

FOREIGN PATENT DOCUMENTS

JP          55-40967          3/1980

(Continued)

OTHER PUBLICATIONS

"In Situ Interfacial Mass Detection With Piezoelectric Transducers", Michael D. Ward et al., Science, vol. 249, Issue 4972, Aug. 31, 1990, pp. 1000-1007.

(Continued)

*Primary Examiner*—Hezron Williams
*Assistant Examiner*—Rose M. Miller

(57) ABSTRACT

A transducer-based sensor system, including a transducer array having a plurality of transducers, a selector coupled with the transducer array and an output processing subsystem. Defined between each transducer and the output processing subsystem is an output transmission path associated with the individual transducer. The selector is configured to apply control signals to the transducer array to cause the array to have at least one selected transducer and at least one unselected transducer. The system is configured so that, for a selected transducer, the output transmission path for that transducer is enabled, so as to permit output signals to be transmitted from the selected transducer to the output processing subsystem. The system is further configured to isolate any unselected transducers, by disabling the output transmission path for such transducers, to thereby prevent transmission of output signals to the output processing subsystem.

9 Claims, 8 Drawing Sheets

U.S. PATENT DOCUMENTS

| | | | |
|---|---|---|---|
| 5,932,807 A | 8/1999 | Mallart | |
| 6,047,162 A * | 4/2000 | Lazaris-Brunner et al. | 455/12.1 |
| 6,055,861 A * | 5/2000 | Banta et al. | 73/626 |
| 6,125,271 A * | 9/2000 | Rowland, Jr. | 455/313 |
| 6,144,332 A | 11/2000 | Reindl et al. | |
| 6,306,090 B1 * | 10/2001 | Wilk | 600/439 |
| 6,321,588 B1 * | 11/2001 | Bowers et al. | 73/24.01 |
| 6,419,633 B1 * | 7/2002 | Robinson et al. | 600/443 |
| 6,600,252 B1 * | 7/2003 | Nguyen | 310/309 |
| 2001/0031025 A1 * | 10/2001 | Nguyen | 375/349 |
| 2002/0011761 A1 | 1/2002 | Takeuchi et al. | |
| 2002/0156414 A1 * | 10/2002 | Redding | 604/22 |
| 2003/0149359 A1 * | 8/2003 | Smith | 600/437 |
| 2004/0064051 A1 * | 4/2004 | Talish et al. | 600/459 |

FOREIGN PATENT DOCUMENTS

| | | |
|---|---|---|
| WO | WO 01/02857 | 1/2001 |

OTHER PUBLICATIONS

"A Novel Immunosensor for Herpes Viruses", Bernd Konig et al., Analytical Chemistry, vol. 66, No. 3, Feb. 1, 1994, pp. 341-344.

"Piezoelectric Mass-Sensing Devices as Biosensors—An Alternative to Optical Biosensors?", Andreas Janshoff et al., The Quarz-Crystal Microbalance in Life Science, Amer. Chem. Int. Ed. 2000, 39, pp. 4004-4032.

"'Hearing' Bond Breakage, Measurement of Bond Rupture Forces Using a Quartz Crystal Microbalance", F. N. Dultsev et al., Langmuir 2000, 16, pp. 5036-5040.

"Listening for Viral Infection", Erica Ollmann Saphire et al., Nature Biotechnology, Sep. 2001, vol. 19, pp. 823-824.

"Direct and Sensitive Detection of a Human Virus by Rupture Event Scanning", Matthew A. Cooper et al., Nature Biotechnology, Sep. 2001, vol. 19, pp. 833-837.

* cited by examiner

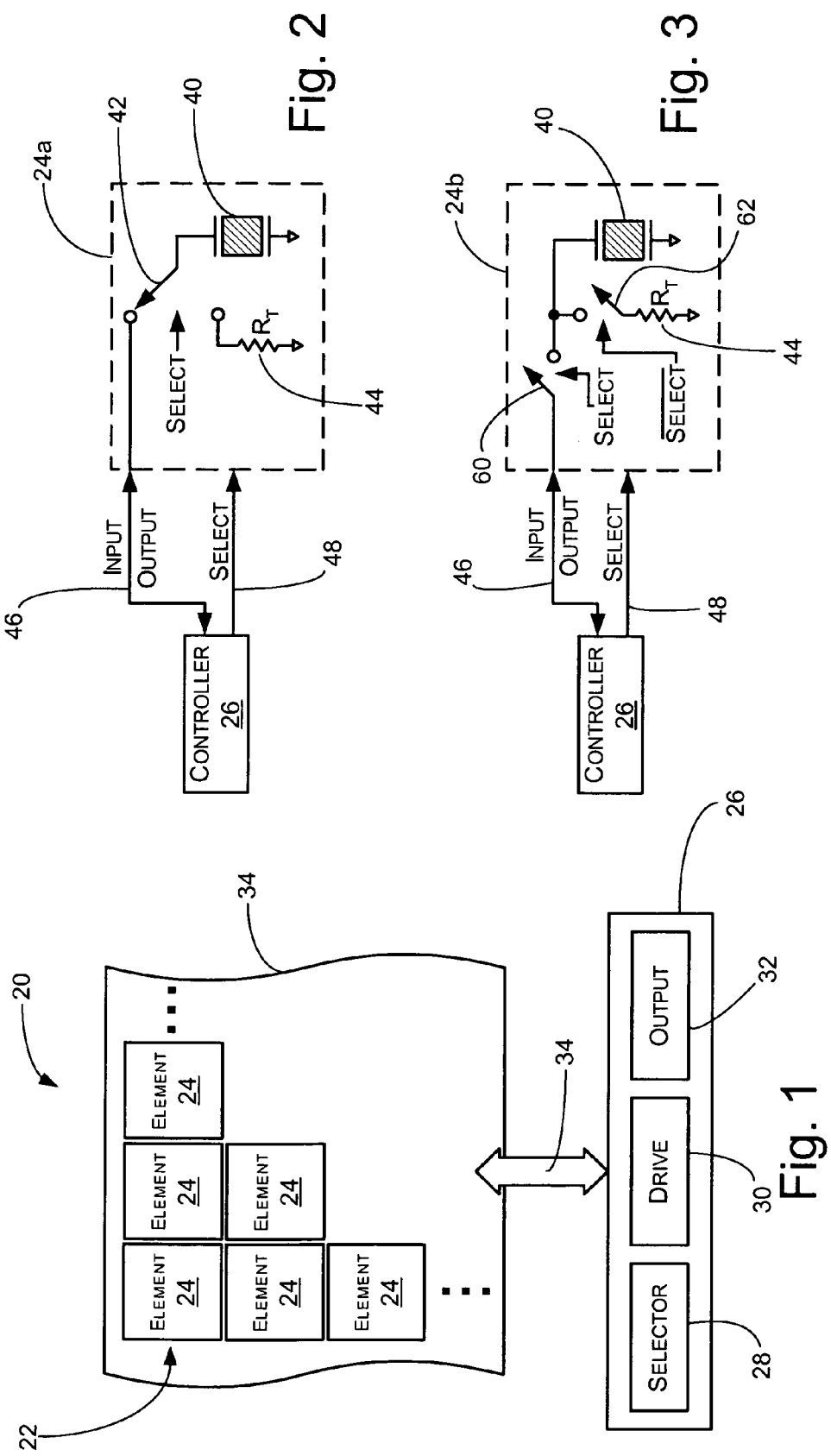

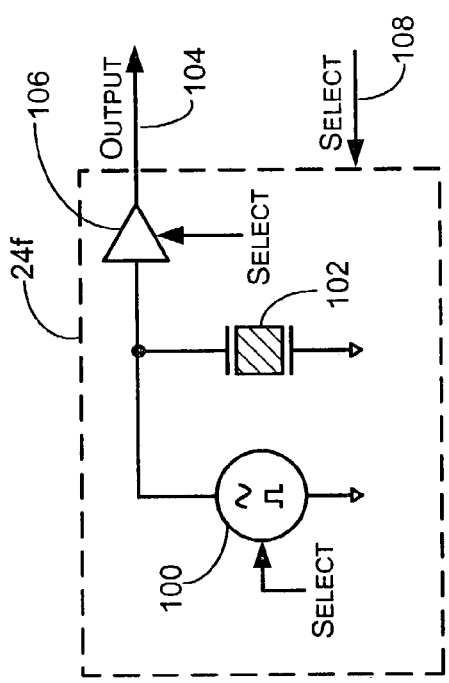
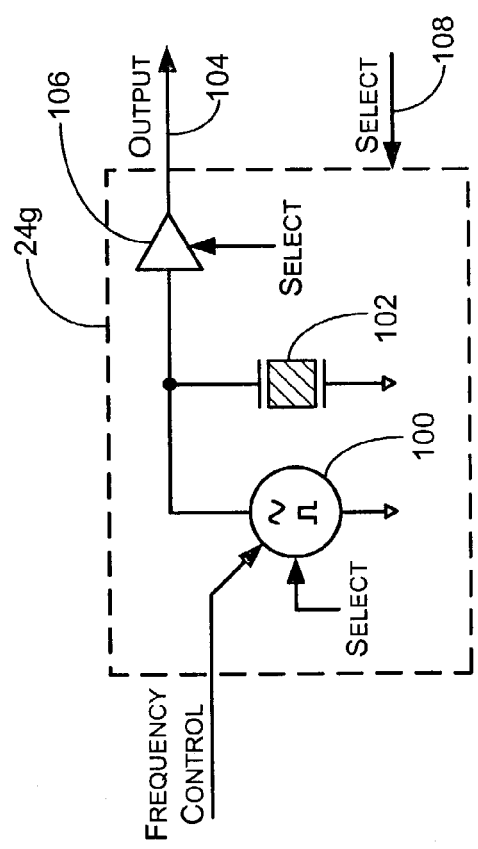

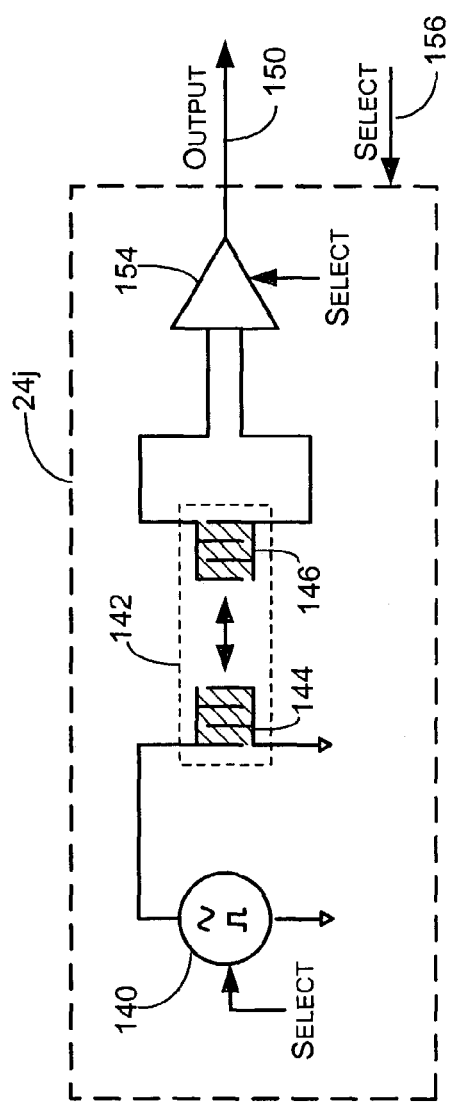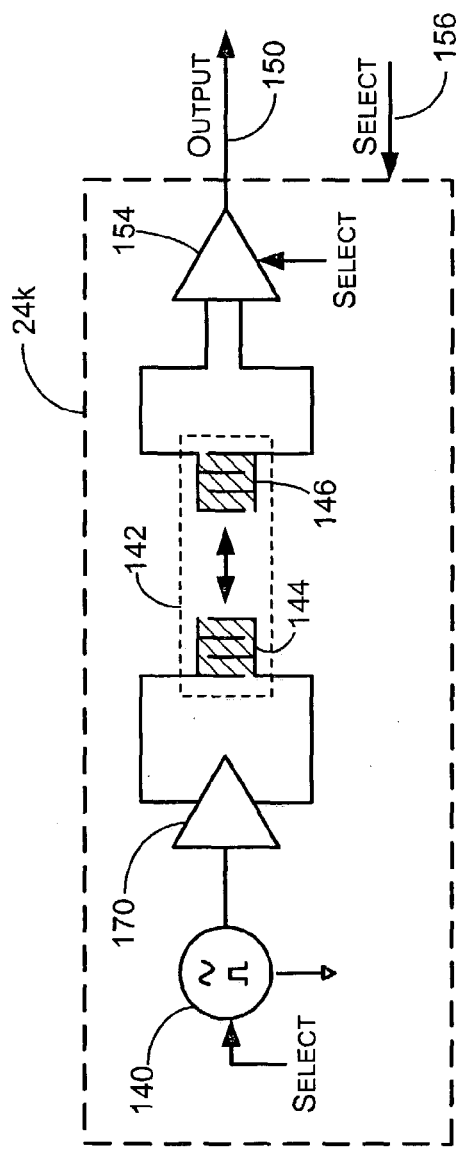

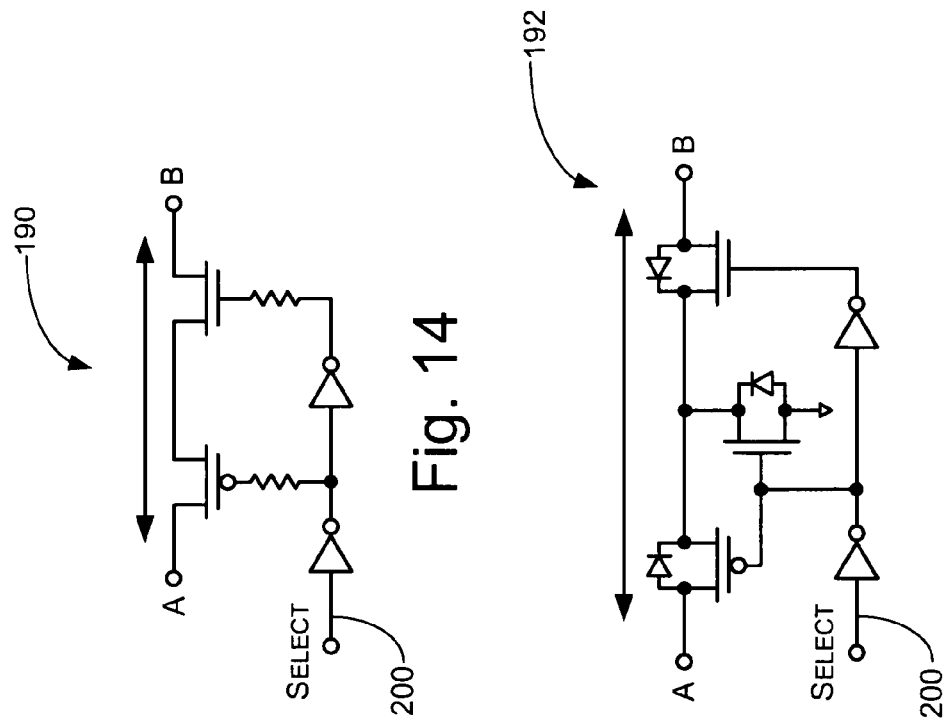
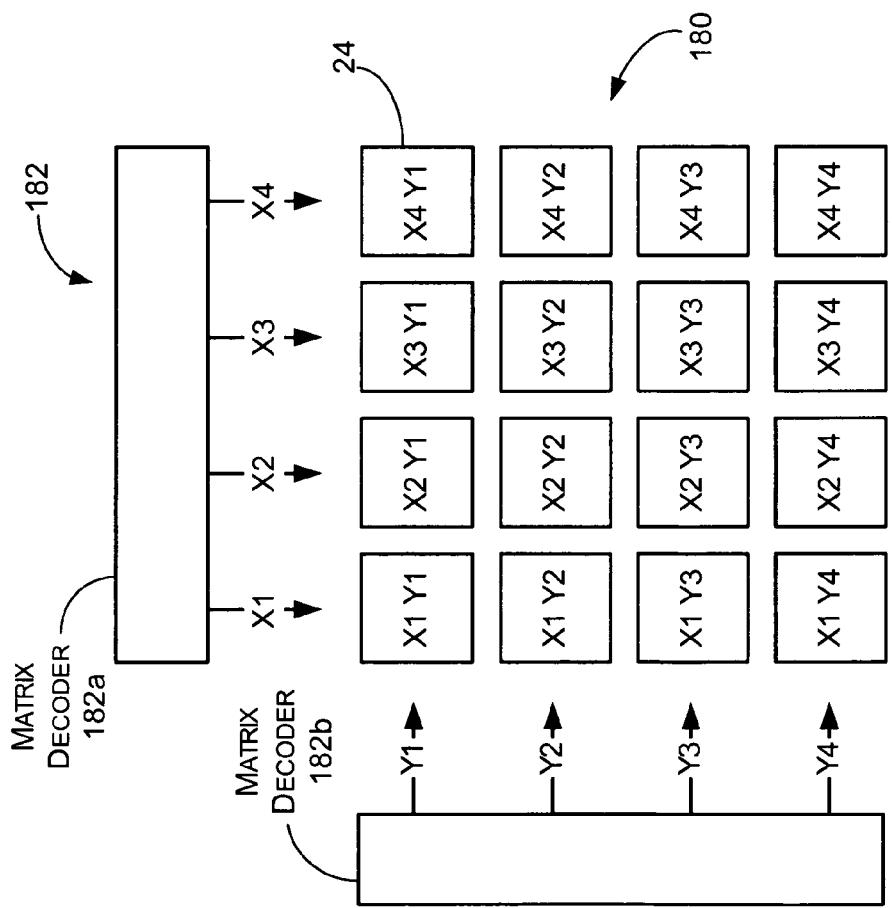

MULTIPLE-TRANSDUCER SENSOR SYSTEM AND METHOD WITH SELECTIVE ACTIVATION AND ISOLATION OF INDIVIDUAL TRANSDUCERS

BACKGROUND

Transducer devices are used in a variety of applications to transfer energy between electrical systems and mechanical systems. Quartz crystal microbalance (QCM), for example, is a transducer-based technology that may employ piezoelectric transducers in various configurations to perform sensing functions. QCM technology takes advantage of the fact that the resonant frequency of a transducer typically varies with the effective mass of the transducer. Accordingly, when portions of a sample material bind to the transducer, the mass of the bonded sample material can be detected by monitoring the resonant frequency of the vibrating mass.

A related technology is rupture event scanning (RES), in which transducers may be employed to produce mechanical energy to break bonds within a sample material. In addition to providing energy to break the bonds, the transducers may be used as sensors to analyze acoustic events (e.g., a pressure wave) that can occur when bonds break. Different types of bonds have unique properties that produce distinctive acoustic events. The bonds can be identified and analyzed by using various techniques to study the acoustic events.

Transducer-based sensor systems often include multiple transducer devices to perform sensing operations on a sample. In many such systems, each transducer is associated with or positioned near a corresponding portion of the sample to be tested. Typically, the transducers are coupled to supporting components that are shared among the transducers, such as drive signal generators, components for processing outputs, etc. The interconnections between the transducers and these shared components, the close proximity of the transducers, and other factors can lead to crosstalk, stray capacitance and inductance, unwanted transmission line effects, and/or other sources of noise. These factors can complicate efforts to obtain output signals for the individual transducers employed in the system.

SUMMARY

The present description provides for a transducer-based sensor system and a method for performing sensing operations on a sample. The system includes a transducer array having a plurality of transducers, a selector coupled with the transducer array and an output processing subsystem. Defined between each transducer and the output processing subsystem is an output transmission path associated with the individual transducer. The selector is configured to apply control signals to the transducer array to cause the array to have at least one selected transducer and at least one unselected transducer. The system is configured so that, for a selected transducer, the output transmission path for that transducer is enabled, so as to permit output signals to be transmitted from the selected transducer to the output processing subsystem. The system is further configured to isolate any unselected transducers, by disabling the output transmission path for such transducers, to thereby prevent transmission of output signals to the output processing subsystem.

BRIEF DESCRIPTION OF THE DRAWINGS

FIG. 1 schematically depicts an embodiment of a transducer-based sensor system according to the present description, including a transducer array with plural elements.

FIGS. 2–12 schematically depict various embodiments of an array element that may be employed in connection with the transducer array of FIG. 1 and the systems and methods of the present description.

FIG. 13 depicts an exemplary array and an embodiment of a decoding mechanism that may be employed in connection with selecting array elements.

FIGS. 14 and 15 depict exemplary switching mechanisms that may be employed with the array element embodiments of FIGS. 2–12.

DETAILED DESCRIPTION

Figure 5:
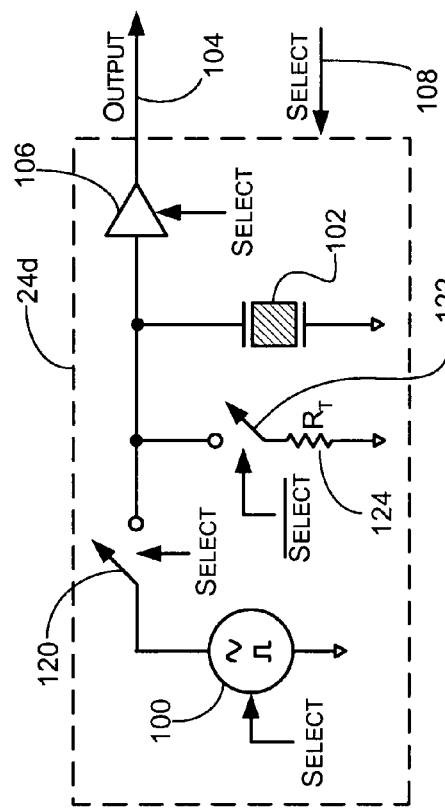
Figure 6:
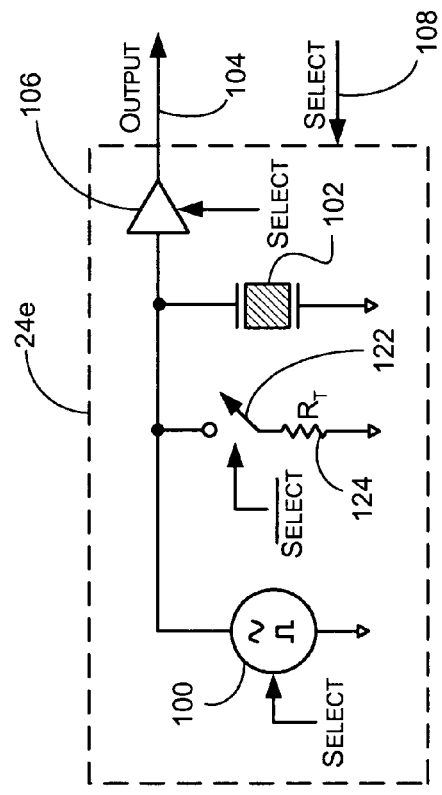

The following description relates to systems, devices and methods in which a transducer is employed to obtain information about matter secured to or in proximity with the transducer. For purposes of illustration only, the description will focus primarily on rupture event scanning (RES) and quartz crystal microbalance (QCM) applications.

FIG. 1 depicts an embodiment of a sensor system 20 according to the present description. System 20 includes a transducer array 22 having plural array elements 24, which typically include at least one transducer. As indicated, transducer array 22 typically is operatively coupled with a controller 26, which may include a selector 28, a drive signal generator 30 and an output processing subsystem 32. Transducer array 22 and controller 26 may be operatively coupled via a bus, electrical network, wireless connection, or any other suitable link, via which various signals 34 may be exchanged, including input/output signals, control signals and the like.

Transducer array 22 typically includes a plurality of transducers that may be placed in operative contact with a sample material 34. System 20 may be configured to perform various sensing operations on sample material 34. System 20 may be implemented, for example, to perform rupture event scanning (RES) or quartz crystal microbalance (QCM) analyses on sample material 34, using piezoelectric crystals, quartz crystals, surface acoustic wave (SAW) devices, or other types of transducers. The transducers may take a variety of configurations, and may be implemented in different sizes and shapes, and with different materials, as desired and appropriate for a given application. In some embodiments, the transducers are implemented within a microchip as an array of piezoelectric crystals, or as an array of surface acoustic wave devices, surface-skimming bulk wave devices, Rayleigh devices or Love-wave devices. Combinations of bulk wave and surface wave devices may be employed, and/or transducer devices that exhibit both surface and bulk modes of operation. In addition, non-piezo transducers may be employed, such as micromachined resonator devices, F-Bar resonators, etc.

During operation, drive signals typically are applied from drive signal generator 30 to one or more transducers within array 22. The transducers move (e.g., mechanically oscillate) in response to application of these drive signals. Typically, movement of the transducers is dependent not only upon characteristics of the activating drive signals, such as frequency and amplitude, but also upon the physical characteristics of the transducer and/or upon physical phenomena occurring around the transducer. For example, the response of a transducer to a given activation signal will depend on the resonant frequency of the transducer. Resonant frequency, in turn, varies with the mass of the transducer. Accordingly, a transducer's movements in response to a given drive signal will be affected by mass that is affixed to the transducer. Variations in mass, as would occur when matter dislodges from a transducer, will therefore produce variation in the physical response of the transducer to a given drive signal.

In addition, breaking of bonds within sample 34 can produce a sonic event (also referred to as an acoustic event) that can affect the movement of a transducer. Specifically, in certain RES implementations, transducers may be prepared with a binding partner material and a candidate component material to be tested. Typically, the binding partner will be affixed to the transducer and the component to be tested will be introduced or otherwise brought into contact with the binding partner. If the component to be tested has sufficient affinity for the immobilized binding partner material (e.g., an affinity between an antigen and a corresponding antibody within the binding partner material), then a bond will form.

The transducer may then be oscillated by applying drive signals to the transducer from controller 26 (e.g., from drive signal generator 30). Application of the drive signal typically creates a reciprocating mechanical oscillation, which in turn produces an electrical output that may be analyzed by output processing subsystem 32. As the transducer oscillates in response to application of the drive signal, bonded particles within sample material 34 (e.g., antibodies and antigens) experience an acceleration, and thus a force, which is proportional to the energy imparted by the applied drive signal. When this force is equal to the force of the bond (e.g., the bond between an antibody and antigen), the bond breaks. Breaking of the bond produces an acoustic event that yields a unique acoustic signature in the output that represents and is associated with the unique binding force(s) between the bonded components (e.g., between the particular antibody and antigen).

Regardless of the particular configuration or application, physical movement of the transducers produces an electrical output signal that may be applied to and processed by controller 26, typically at output processing subsystem 32. This processing may be performed to analyze sample material 34, or respective portions thereof. RES analysis may be employed, for example, to determine whether sample material 34 contains a particular antigen, pathogen or other component of interest, by detecting and analyzing acoustic events that occur during oscillation of the transducer.

Controller 26 may be configured in many different ways, but typically is implemented to include a processor and memory that is operatively coupled with transducer array 22. Controller 26 may perform various functions, including performing overall system control; conducting sequential control of various system components; generating and applying drive signals to the transducer array in order to mechanically excite the transducers; controlling the energy imparted by the drive signals by controlling the amplitude and/or duration of the drive signals; detecting and/or obtaining resonant frequencies of the transducers, including initial frequencies and subsequent frequencies (e.g., after mass has been dislodged); sampling output from the transducers in response to application of the drive signals; storing the digitized output samples from the transducers; performing frequency domain transformations as appropriate on the sampled data; filtering or otherwise removing extraneous or unwanted portions of the sampled data; and comparing remaining portions of the sampled data to stored data, such as bond adhesion tables, to determine whether particular rupture events occurred. Several of these functions will be described in more detail below. It should be understood that the recited functions are illustrative only, and should not be interpreted in a limiting or restrictive sense. The processor and memory may be implemented in a variety of ways and configured as desired to suit the needs of a particular application.

From the above, it should also be appreciated that FIG. 1 is a schematic depiction, and that the depicted components may be arranged in a variety of different configurations. Sample material 34 may, for example, be provided in solution form and positioned to contact an operative surface of the transducers. The solution may be provided in a single well or container, or may be compartmentalized into portions corresponding to one or more transducers within array 22. Additionally, or alternatively, sample material 34 may be provided in discrete portions, with each portion corresponding to an individual transducer. For example, each transducer may be prepared in advance with a discrete portion to be tested. Also, sub-components of controller 26 may be integrated into a single component (e.g., a microchip) as shown, or may be provided as separate discrete components. Similarly, controller 26 (and/or its subcomponents) may be integrated with transducer array 22 on a single chip or silicon device, or may be provided separately.

The following co-pending U.S. patent applications provide further examples of transducer-based systems and methods having features that may be employed in connection with the systems and methods described herein: U.S. patent application Ser. No. 10/286,071 "Transducer-Based Sensor System with Multiple Drive Signal Variants" by Daniel R. Blakley, filed Oct. 31, 2002; U.S. patent application Ser. No. 10/355,396 "Transducer-Based Sensor System" by Daniel R. Blakley, filed Jan. 31, 2003; and U.S. patent application Ser. No. 10/356,084 "Sensor System and Method Employing Shared Transducer Elements" by Daniel R. Blakley, filed Jan. 31, 2003. The disclosures of these patent applications are incorporated herein by this reference, in their entirety and for all purposes.

Most of the exemplary systems discussed above involve multiple transducers. Use of multiple transducers is often desirable in order to provide faster scanning. When multiple transducers are employed, it may be advantageous to connect more than one transducer to input or output systems, and/or to otherwise share various components among the transducers. For example, in FIG. 1, a single output processing subsystem 32 is employed to receive and process output signals from all of the transducer array elements 24. Sharing of components can simplify design and reduce physical space occupied by the sensor system.

Typically, it will be desirable to obtain noise-free output signals corresponding to individual transducers within array 22. Multiple transducer configurations can, however, produce certain effects that may lead to problematic output noise if not addressed. Many of these effects result from multiplexing and/or from direct or indirect electrical couplings between system components.

Often, the transducers are high impedance devices that are operated at high frequencies. Accordingly, the transducers may be susceptible to noise pickup and various undesired transmission line effects when the array is multiplexed to selectively activate individual transducers or subsets of transducers. Multiplexing may cause higher inductance as well as distributed capacitance on some of the transducers in a multiplexed array, particularly for transducers at greater distances from the multiplexing device. Also, non-terminated or partially terminated transmission lines in the multiplexed array can produce signal reflections, which can be another source of undesired noise in the system output.

Accordingly, system 20 may be configured to select transducers within transducer array 22, such that the array typically will include a selected transducer or transducers, and an unselected transducer or transducers. For the selected transducers, system 20 is configured to enable a transmission path between the selected transducer and the output processing subsystem. Enabling of the transmission path permits transmission of output signals from the selected transducer to controller 26 (e.g., to output processing subsystem 32).

In contrast, system 20 is configured so that any unselected transducers within array 22 are isolated from controller 26, and thus from output processing subsystem 32. Typically, this is accomplished by disabling the transmission path between the unselected transducer and the output processing subsystem. Accordingly, output signals are prevented from being transmitted from the unselected transducer to the output processing subsystem.

A selector 28 (FIG. 1) may be provided to facilitate selection and un-selection of portions of array 22. Typically, selector 28 applies a select signal (e.g., a logical HI voltage) to particular elements 24 within array 22 having transducers that are to be selected for activation. In the exemplary array elements described below, the elements include select inputs for receiving the select signal. For unselected array elements, the select inputs may be maintained at an unselect level or signal (e.g., a logical LO voltage), which may be applied from selector 28. Typically, as will be explained below, the enabling and disabling of transmission paths for transducers within array 22 is controlled in response to the levels presented at the select inputs of the elements 24 in the array.

FIGS. 2–12 schematically depict various alternate embodiments of array elements 24 shown in system 20 of FIG. 1. The embodiments are denoted with the general reference number 24, and are individually designated with letter suffixes: 24a, 24b, 24c, etc. Several of the embodiments will include similar components. Like elements will be designated with like reference numbers, and will not be repeatedly described, except to note details specific to a particular exemplary configuration.

FIG. 2 depicts an embodiment of an array element 24a that may be employed with system 20 of FIG. 1. As shown, array element 24a may include a transducer device such as piezoelectric crystal 40, a switch 42 and a terminator such as terminating resistance $R_T$(44). Array element 24a is operatively coupled with controller 26 via input/output transmission line 46 and select line 48.

When multiple elements 24a are incorporated into a transducer array (e.g., array 22), the elements may be configured so that input drive signals are applied globally from a global drive signal generator (e.g., drive signal generator 30) along the transmission paths 46 of the respective elements 24a. Multiplexing (e.g., selective activation and deactivation) of selected array elements may be controlled via voltage levels (e.g., HI or LO) applied along the select lines 48 of elements 24a.

In particular, if a given element 24a is selected, the select signal (e.g., logical HI) is applied to select line 48. As shown, the state of switch 42 is dependent upon the voltage on select line 48. Specifically, if the array element is activated (e.g., by logical HI in the depicted example), then switch 42 is put in a state such that the transmission path (e.g., path 46) between crystal 40 and controller 26 is enabled. Accordingly, drive signals from controller 26 (e.g., from global drive signal generator 30) are permitted to pass to piezoelectric crystal 40, thereby mechanically stimulating the crystal (e.g., as part of an RES or QCM operation). Also, any output signals produced as a result of the crystal's movement are permitted to pass along the transmission path to controller 26, where they may be analyzed to obtain information about sample material attached to or near the piezoelectric crystal.

If an unselect signal (e.g., logical LO) is applied, switch 42 is placed in a second state, in which the transmission path between the crystal and controller (e.g., path 46) is disabled. In this and other exemplary embodiments discussed herein, this disabling of the output transmission path is one example of how the unselected transducer may be isolated. Isolation may also be achieved, as in the depicted example, by configuring element 24a so that, when the element is unselected, switch 42 causes piezoelectric crystal 40 to be connected to terminating resistance 44. Terminating resistance 44 typically is selected so as to provide less than or equal to a matched impedance for crystal 40, thereby inhibiting signal reflections and other transmission line effects, which could produce noise in readings being taken from a selected transducer or transducers.

From the above, it should be appreciated that switch 42 is positioned within a transmission path between piezoelectric crystal 40 and controller 26, and within a transmission path between the piezoelectric crystal and terminating resistance 44. In the depicted example, the first transmission path (between the crystal and controller) is enabled when a logical HI voltage is applied along select line 48, thereby pausing the switch to connect the transducer to controller 26. The second path is disabled. Conversely, when a logical LO voltage is applied, the switch connects the transducer to the terminating resistance 44.

In the context of system 20 (FIG. 1), multiple array elements 24a may be employed, with each being coupled to controller 26 via input/output lines 46 and select lines 48. Selector 28 generates signals corresponding to the desired status of each element in the array (e.g., activated or deactivated), and applies those signals along the respective select lines 48 of the array elements. The specific signals may be of any appropriate value, so as to place array elements and their respective transducers in either a selected or unselected state. As discussed above, when an array element 24a is selected, switch 42 connects the transducer (e.g., crystal 40) to the controller. All of the remaining elements within the array are typically unselected, so that the switches 42 for the unselected elements cause the corresponding transducers to be coupled to terminating resistances 44. When disconnected from controller 26 and terminated in this manner, the unselected transducers are less likely to contribute noise (via reflections, other transmission line effects, etc.) into the output reading for the selected transducer, as the corresponding signal is thereby absorbed by the terminating resistance.

Continuing with the above example, it will often be desirable to sequentially select transducers within the array. In such sequential operation, a first element is selected (with all other elements being unselected), and output signals are obtained for the associated transducer. Then a second element is selected, and a third element, and so on, cycling through all the elements of the array.

Instead of selecting transducers individually, as in the sequential example given above, multiple transducers in an array may be selected at one time. For example, in certain sensing applications, adequate noise suppression may be obtained within an array by ensuring that activated transducers are separated by a specified distance. Subject to this constraint, more than one element within the array may be activated, with intervening elements being unselected (e.g., resulting in disabling of the transducer's output transmission path and connecting the transducer to a terminator).

FIG. 3 depicts another embodiment of an array element 24b that may be employed with system 20 of FIG. 1. As with element 24a, element 24b may be coupled with controller 26 via input/output line 46 and select line 48, and may include a piezoelectric crystal 40 and terminating resistance 44. Multiple elements 24b may be employed within an array and operated in the same manner as described with reference to elements 24a. However, instead of a double throw switch, two single throw switches 60 and 62 may be controlled to enable transmission paths between crystal 40 and either controller 26 or terminating resistance 44, depending on whether the array element is selected or not.

Specifically, if the element is selected, switch 60 closes to enable the transmission path between crystal 40 and controller 26, and switch 62 is opened to operatively disconnect the crystal from the terminating resistance. If the element is unselected, switch 62 closes to enable the terminating connection and switch 60 opens to disable the transmission path between the transducer and controller 26.

Figure 4:
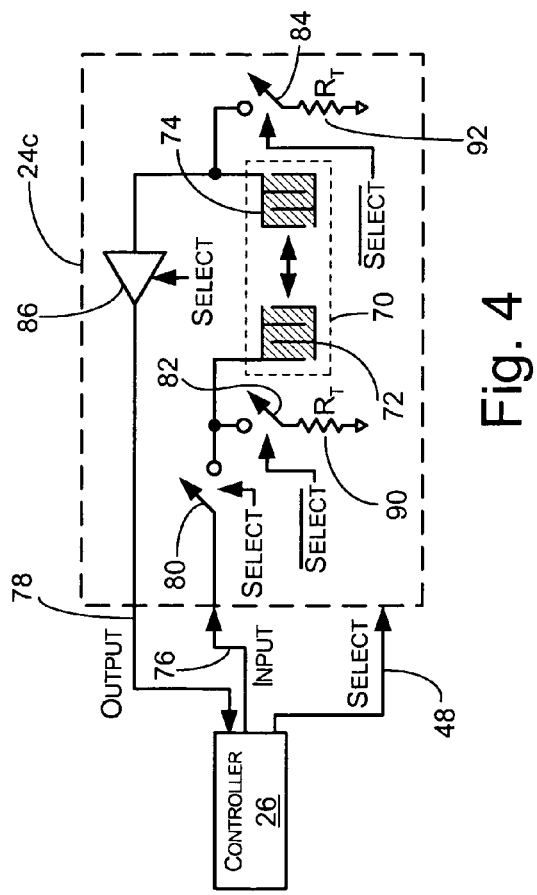

FIG. 4 depicts another embodiment of an array element 24c that may be employed with system 20 of FIG. 1. In contrast to the previous examples, the transducer of the element is implemented as a surface acoustic wave (SAW) device 70 including an emitter element 72 and a receiver element 74. Transmitter 72 and receiver 74 may be constructed from piezoelectric material with interdigitated electrode structures, as in the depicted example. As shown in the figure, element 24c may be coupled with controller 26 via input line 76, output line 78 and select line 48.

During operation, selection of element 24c (e.g., by application of an appropriate signal to select line 48) causes switch 80 to close, switches 82 and 84 to open, and enables amplifier buffer 86. Accordingly, input drive signals (e.g., from drive signal generator 30, shown in FIG. 1) are permitted to pass along input line 76 and be received at emitter 72. Emitter 72 thus generates SAW waves which propagate through a portion of sample material 34 (not shown in FIG. 4) in the vicinity of SAW device 70. The emitted SAW waves, which are affected by sample material 34 (e.g., by rupture events occurring in region between emitter 72 and receiver 74), impinge upon receiver 74 and produce electrical output signals.

As discussed above, selection of element 24c enables buffer amplifier 86. Typically, this places the amplifier in a unity-gain state in which signals are permitted to pass through and out of the element to be received by controller 26. Accordingly, this enables the output transmission path between transducer 70 and the output processing subsystem within controller 26 (e.g., output processing subsystem 32). More specifically, output from receiver element 74 is passed through the amplifier buffer and is received at controller 26 via output line 78.

In contrast, when element 24c is not selected, switch 80 opens, thereby preventing transmission of drive signals from the drive signal generator to the transducer. Switches 82 and 84 close, thereby operatively connecting both sides of SAW device 70 to terminating resistances 90 and 92. As in the previous example, the terminating resistances are selected to damp the transducer's signals, and thereby facilitate its isolation from the rest of the system when unselected. Also, buffer amplifier 86 may be disabled, thereby disabling the output transmission path between the transducer and output processing subsystem 32.

FIGS. 5–8 schematically depict further alternate embodiments of array elements that may be employed with system 20 of FIG. 1. The array elements are respectively designated in these figures as 24d, 24e, 24f and 24g. As indicated, each element may include a local drive signal generator 100 configured to apply drive signals to a transducer such as piezoelectric crystal 102. Quartz crystal resonator 102 may be coupled with output processing subsystem 32 (not shown in FIGS; 5–8) via an output transmission path that includes output line 104, and which may be selectively enabled and disabled via operation of buffer amplifier 106. Each element may be coupled to an external control system, such as selector 28 shown in FIG. 1, via select line 108.

For each of array element embodiments 24d, 24e, 24f and 24g, selection of the element (e.g., by applying a HI signal at input 108) enables local drive signal generator 100, which then outputs a sinusoid or other suitable waveform or signal to drive quartz crystal resonator 102. Selection also activates buffer amplifier 106, so as to enable the transducer output transmission path and permit transmission of output signals to the external processing unit (e.g., output processing subsystem 32). When the array element is not selected, the drive signal generator and output transmission path are disabled. Disabling of the drive signal generator and output transmission path isolates the transducer, by reducing or eliminating the possibility that the unselected transducer will introduce noise into output readings for selected transducers at other positions within array 22.

For the embodiments of FIGS. 5–8, it should be appreciated that the drive signal generator 100 is local, and therefore a global generator, such as generator 30 shown in FIG. 1, may not be needed.

As discussed above, selective enablement and disablement of generator 100 and the transducer output transmission path facilitates suppression of noise, and the obtainment of desired output signals which correspond to selected transducers within a multiple-transducer array. As shown in FIG. 5, additional switches 120 and 122 may be employed to further improve the selective activation and deactivation of array elements. Upon selection of exemplary element 24d, switch 120 is maintained closed, and switch 122 is maintained open. Accordingly, the input path from generator 100 to the transducer (e.g., crystal 102) is enabled, and the path between the crystal and terminating resistance 124 is disabled. Conversely, when the element is not selected, the states of the switches are reversed, such that the crystal is operatively coupled with the terminating resistance and operatively decoupled from generator 100.

In some settings, the implicit isolation achieved through use of a localized, selectively enabled drive signal generator may permit simplification of individual array elements. In element 24e of FIG. 6, for example, switch 122 and terminating resistance 124 are included as in FIG. 5, however switch 120 of FIG. 5 is omitted. Also, as seen in FIGS. 7 and 8, drive signal generator 100 may be configured to present a low impedance to ground when array elements 24f and 24g are in an unselected state. Accordingly, in these embodiments, crystal 102 may be terminated by the output impedance of the deactivated generator, and the switched terminator arrangement of FIGS. 5 and 6 may be omitted.

Also, as seen in FIG. 8, various control signals other than enable/disable controls, such as the depicted frequency control, may be provided to control operation of the local drive signal generator.

Figure 9:
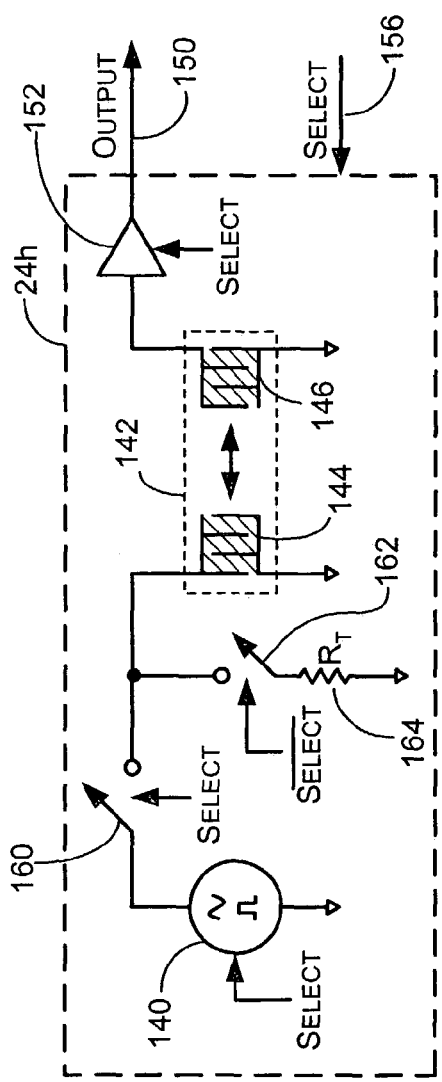
Figure 10:
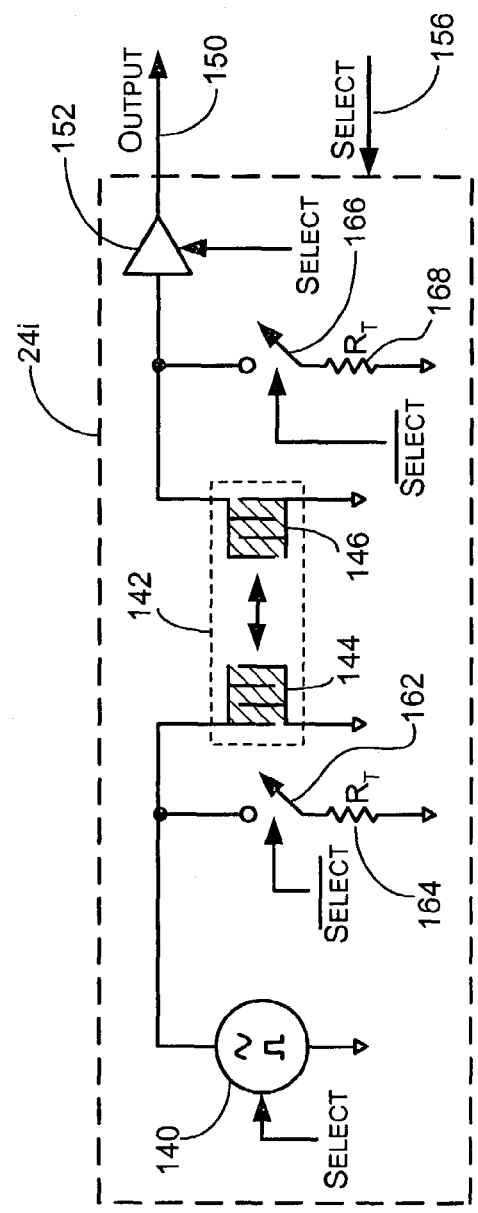

FIGS. 9–12 schematically depict further alternate embodiments of array elements that may be employed with system 20 of FIG. 1. The array elements are respectively designated in these figures as 24h, 24i, 24j and 24k. As indicated, each element may include a local drive signal generator 140 configured to apply drive signals to a transducer such as SAW device 142, which may include an emitter 144 and receiver 146. Saw device 142 may be coupled with output processing subsystem 32 (not shown in FIGS. 9–12) via an output transmission path that includes output line 150, and which may be selectively enabled and disabled via operation of a buffer amplifier. In the embodiments of FIGS. 9 and 10, the buffer amplifiers are designated at 152. Differential buffer amplifiers 154 are employed in the embodiments of FIGS. 11 and 12, as will be explained below. The array element embodiments shown in FIGS. 9–12 may be coupled to an external control system, such as selector 28 shown in FIG. 1, via select line 156.

Referring still to FIGS. 9–12, selection of the respective element enables local drive signal generator 140 and enables the output transmission path associated with SAW device 142. Conversely, when the array element is not selected, generator 140 and the transducer output path may be disabled, in order to reduce noise and facilitate readings for the array elements which are selected.

As in the embodiments of FIGS. 5–8, various additional components and features may be optionally employed to facilitate selection/de-selection of array elements 24h, 24i, 24j and 24k. For example, a switch 160 may be coupled between drive signal generator 140 and SAW device 142, as indicated in FIG. 9. Switch 160 operates similar to switch 120 (FIG. 5) so as to enable application of drive signals to the transducer upon selection of element 24h (e.g., by application of a HI signal to select line 156).

Either or both sides of SAW device 142 may be operatively coupled to a terminating load when the array element is not selected. For example, the embodiment of FIG. 9 includes a switch 162 and terminating resistance 164 on the input side of SAW device 142. The embodiment of FIG. 10 additionally includes a switch 166 and terminating resistance 168 on the output side of SAW device 142.

As with the embodiments of FIGS. 7 and 8, in some settings, the isolation achieved by selectively enabling the generator and transducer output path may be sufficient so as to not require switched terminators, as demonstrated by the omission of these structures from the exemplary embodiments of FIGS. 11 and 12. As indicated above, drive signal generator 140 may be configured in such a case so that the transducer (e.g., SAW 142) is terminated by the output impedance of the deactivated generator 140.

Referring particularly to FIGS. 11 and 12, SAW device 142 may be implemented in differential configurations. In exemplary array elements 24j and 24k, receiver element 146 is connected to amplifier 154 as a differential input, instead of to ground. This provides SAW device 142 with a balanced output and facilitates common mode rejection at the amplifier to provide further noise suppression benefits. Additionally, or alternatively, the input side of SAW device 142 may be provided with a differential amplifier 170, which in some settings may facilitate use of higher amplitude signals and improve noise suppression.

Any type of decoding or other logic scheme may be employed to facilitate selection of array elements. FIG. 13 depicts exemplary array 180 of elements 24. Elements 24 each include at least one transducer and may be of any desired construction, including the constructions previously discussed with reference to the element embodiments of FIGS. 2–12. As indicated, elements 24 may be arranged as a two-dimensional matrix having sixteen elements 24 (though any other practicable number many be employed). In the depicted example, the elements are selected using a matrix-type decoding scheme.

Specifically, matrix decoder 182 may be implemented as part of controller 26 shown in FIG. 1 (e.g., as part of selector 28), and may include a first section 182a having four outputs: X1, X2, X3 and X4. Decoder 182 may also include a second section 182b having four additional outputs: Y1, Y2, Y3 and Y4. Each element 24 within the array is coupled to two of the outputs, with individual array elements being designated in the figure according to the specific decoder connections. Starting in the upper left corner and moving to the right, the first element is connected to the X1 and Y1 decoder outputs, the second element is connected to the X2 and Y1 decoder outputs, and so on. Typically, an individual element is selected, or activated, according to an AND of the two respective inputs. Thus, the first element would be selected, for example, when both the X1 and Y1 outputs are at logical HI levels.

FIGS. 14 and 15 depict examples of switching mechanisms that may be employed with the systems and methods described herein. As discussed with reference to the previously described embodiments, a variety of switching technologies may be employed., In many cases, it will be desirable to employ RF switching technologies, such as absorptive RF switches, CMOS RF transmission gates, nano-relays, and PIN diode (bulk switching) RF switches. FIGS. 14 and 15 depict CMOS RF transmission gate switches 190 and 192. Switches 190 and 192 have a single pole, single throw configuration, and may be implemented in connection with the embodiments shown in FIGS. 1–13.

In both examples, voltage levels applied along select line 200 control whether current is permitted to flow through the transistors coupled between terminals A and B. For example, if either of the exemplary switches were used as switch 60 in FIG. 3, applying a HI level to line 200 would close the switch and thereby enable the input/output transmission line between piezoelectric crystal 40 and controller 26. Referring still to FIGS. 14 and 15, in switch 190, two transistors are employed to compensate for back body diode leakage and capacitance from drain to source. A third transistor may be added, as in switch 192, which is turned on when the first two transistors are turned off, to minimize path leakage between terminals A and B.

Furthermore, it may be desirable in some settings to cascade the switches employed with the systems and methods of the present description. For example, in an array of elements 24b (FIG. 3), the overall capacitance seen by the system will be the sum of the capacitances of each of the switches 60 and the piezoelectric crystals 40. This value can be reduced by cascading switches 60 into hierarchical levels of switches, where a lower level of switches is activated by a higher level switch. In some settings, such a cascading arrangement can decrease overall capacitance and thereby provide improved frequency response and reduced crosstalk.

Figure 16:
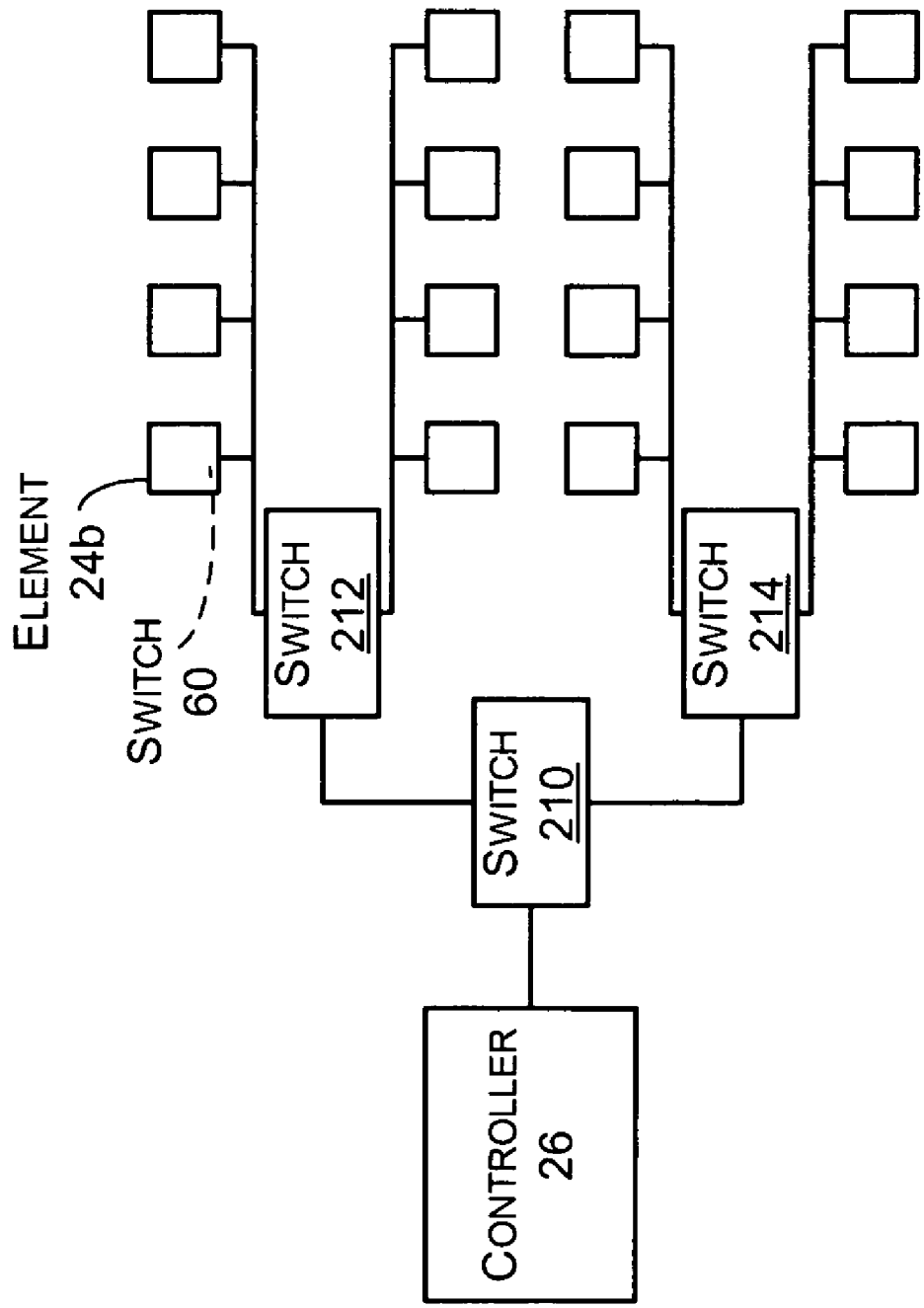
FIG. 16 depicts an embodiment of an exemplary cascaded switch arrangement that may be employed with the sensor systems of the present description.

FIG. 16 depicts an example of an array of elements 24b employing an exemplary cascaded switch configuration. As shown, the exemplary array contains sixteen array elements 24b, each having an associated switch 60, as described with reference to FIG. 3. Higher level switches 210, and 212 and 214 respond to control signals (e.g., provided from controller 26) in order to control selection of individual array elements, and thereby activate operative connections between controller 26 and the selected array element. For example, to select a given one of the uppermost row of elements 24b, switch 210 enables the transmission pathway from controller 26 to switch 212, and switch 212 enables the transmission pathway to the upper row of elements 24b. The individual element may then be selected via operation of its corresponding switch 60. It should be appreciated that a variety of different cascading arrangements may be employed, and cascading may be used in conjunction with any of the systems described herein.

Figure 17:
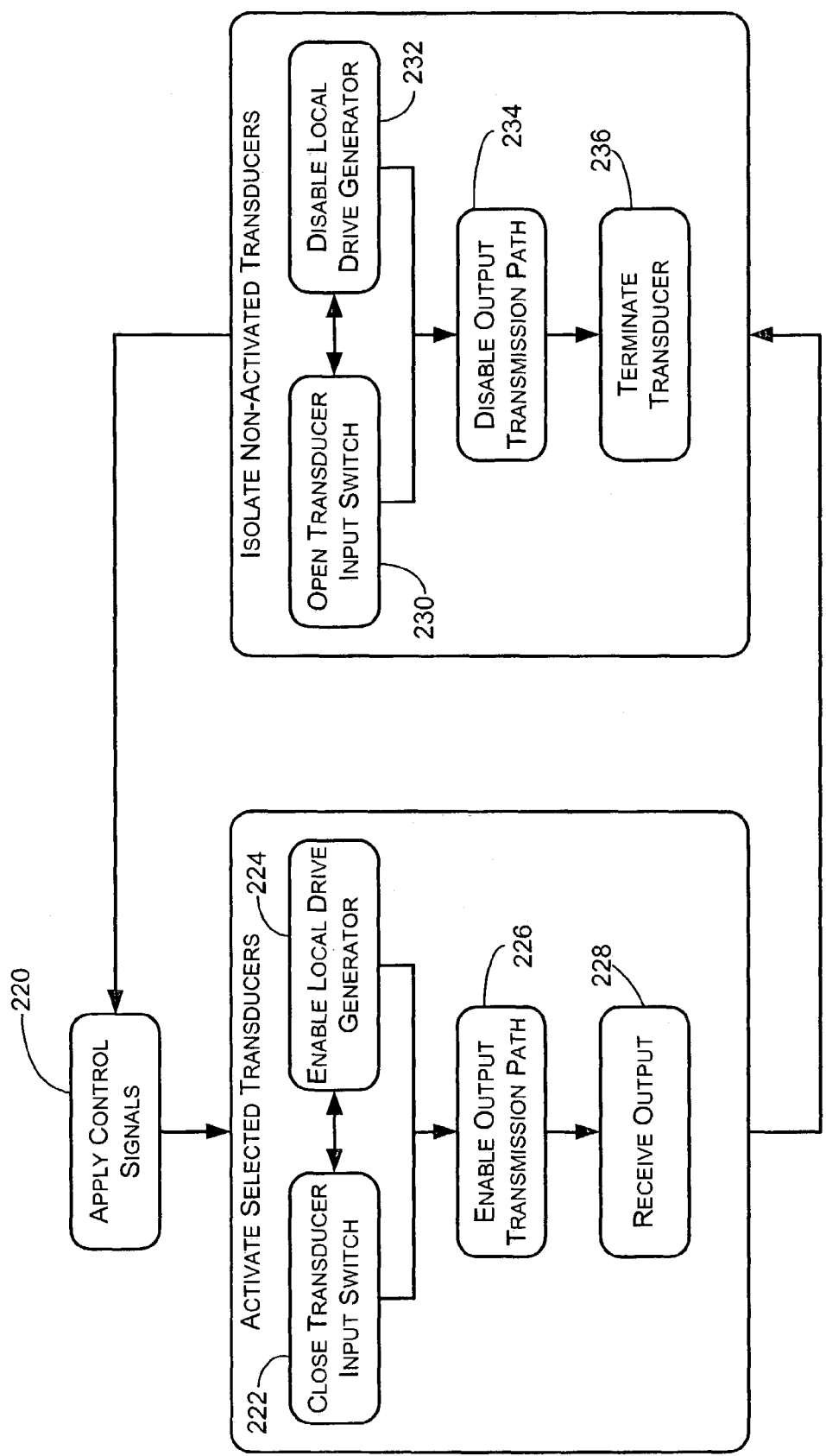
FIG. 17 depicts an embodiment of a transducer-based sensor method of the present description employing a transducer array having multiple array elements that are selectively activated and isolated over time.

It will also be appreciated that the present description encompasses methods for performing sensing operations using a transducer array. FIG. 17 depicts an example of such a method. As shown at 220, the method may include applying control signals in order to activate selected portions of the array. Typically, as described with respect to the above embodiments, at any given time the array will include at least one activated transducer, and one or more non-activated transducers. The control signals may be provided from any suitable source, such as from previously described controller 26 and selector 28.

For the selected, or activated, transducers, the method may further include causing drive signals to be applied to the transducers, in order to mechanically stimulate the transducers. This may include, for each such selected transducer, closing an input switch to the transducer and/or enabling a local drive signal generator associated within transducer, as shown at 222 and 224. Exemplary embodiments in which a transducer input switch is closed upon selected of the array element are shown in and described with respect to FIGS. 2–5 and 9. Exemplary embodiments in which a local drive signal generator is activated upon selection of the array element are shown in and described with respect to FIGS. 5–12.

The method may further include, for each selected transducer, enabling an output transmission path associated with the transducer, and receiving the output signal for the transducer (e.g., at controller 26). These steps are shown at 226 and 228. Referring to the exemplary embodiments above, the output transmission path is enabled in FIGS. 2 and 3 by closing a switch coupled between piezoelectric crystal 40 and controller 26. In the embodiments of FIGS. 4–12, a buffer amplifier between the transducer and controller 26 is controlled to selectively permit transmission of output from the transducer.

The non-activated transducers typically are isolated, as in several of the exemplary embodiments discussed above, so as to inhibit coupling of noise from the non-activated transducers into output being obtained for the activated transducer(s). Specifically, the method may include preventing drive signals from being applied to the non-activated transducers. This may include opening an input switch between a drive signal source and the transducer, as shown at 230 (FIG. 16) and implemented in the exemplary embodiments of FIGS. 2–5 and 9. Additionally, or alternatively, a local drive source for the transducer may be disabled, as shown at 232 and implemented in the exemplary embodiments of FIGS. 5–12.

Isolation of non-activated transducers may further include disabling the transducer output transmission path, as shown at 234 and implemented in the exemplary embodiments of FIGS. 2–12. Additionally, each isolated transducer may be coupled with a terminating impedance, as shown at 236, in order to terminate the transducer and prevent unwanted signal reflections, transmission line effects, etc. that may lead to noise contributions in the output for the selected transducers.

After outputs are obtained for the selected transducer or transducers, the control signals may be varied (e.g., at 220) so as to select and isolate different transducers in the array. Indeed, control signals may be varied so as to repeatedly cycle through and activate all of the transducers in the array. Typically, at any given time, only one transducer or a subset of the transducers are activated, and the remaining transducers are isolated and terminated in order to reduce or eliminate noise in the output obtained for the selected transducer(s). Also, it should be appreciated that the various steps of the depicted method may be performed simultaneously and/or in any appropriate sequence.

While the present embodiments and method implementations have been particularly shown and described, those skilled in the art will understand that many variations may be made therein without departing from the spirit and scope defined in the following claims. The description should be understood to include all novel and non-obvious combinations of elements described herein, and claims may be presented in this or a later application to any novel and non-obvious combination of these elements. Where the claims recite "a" or "a first" element or the equivalent thereof, such claims should be understood to include incorporation of one or more such elements, neither requiring nor excluding two or more such elements.

What is claimed is:

1. A transducer-based sensor system, comprising:
   a transducer array including a plurality of transducers, where at least one transducer in the transducer array is configured to have a sample material attached thereto, and where the transducers are surface acoustic wave devices;
   an output processing subsystem coupled with the transducer array; and
   a selector coupled with the transducer array and configured to selectively activate transducers within the transducer array by applying an enabling signal to the transducer array for at least one, but less than all, of the transducers, such that the transducer array includes at least one selected transducer and at least one unselected transducer, where:
   for a selected transducer, application of the enabling signal enables a
   transmission path between the selected transducer and the output processing
   subsystem, thereby permitting output signals to be transmitted from the selected
   transducer to the output processing subsystem,
   where the transducer array includes a local drive signal generator for each transducer of the transducer array, and where activating one or more of the transducers within the transducer array includes closing a switch between the transducer to be activated and the local drive signal generator associated with such transducer.

2. A transducer-based sensor system, comprising:
   a transducer array including a plurality of transducers configured to be placed into operative proximity with a sample material, and configured to produce electrical output based upon drive signals applied to the transducers and upon the sample material, where at least one transducer in the transducer array is configured to have a sample material attached thereto;
   an output transmission path associated with each transducer, each output transmission path being defined between its associated transducer and an output processing subsystem configured to receive electrical output from the transducers; and
   a selector configured to control activation and deactivation of portions of the transducer array by enabling and disabling the output transmission paths such that each output transmission path is either enabled, thereby allowing transmission of electrical output from the respective transducer to the output processing system, or disabled, thereby preventing transmission of electrical output from the respective transducer to the output processing system; and a local drive signal generator for each transducer, where the selector is configured to control transducer activation for each transducer by permitting drive signals to be applied from the local drive signal generator to the transducer if the output transmission path for transducer is enabled, and by preventing drive signals from being applied from the local drive signal generator to the transducer if the output transmission path for the transducer is disabled;

where each local drive signal generator is coupled with and controlled by the selector such that the local drive signal generator is enabled if the output transmission path of its associated transducer is enabled; and where for each transducer, a switch is coupled between the transducer and the transducer's local drive signal generator, the switch being configured to close if the output transmission path, for the tranducer is enabled, and to open if the output transmission path for the transducer is disabled.

3. A transducer-based sensor system, comprising:

a transducer array including a plurality of transducers configured to be placed into operative proximity with a sample material, and configured to produce electrical output based upon drive signals applied to the transducers and upon the sample material, where at least one transducer in the transducer array is configured to have a sample material attached thereto, and where the transducers are configured to provide both bulk wave and surface wave modes of operation;

an output transmission path associated with each transducer, each output transmission path being defined between its associated transducer and an output processing subsystem configured to receive electrical output from the transducers; and a selector configured to control activation and deactivation of portions of the transducer array by enabling and disabling the output transmission paths such that each output transmission path is either enabled, thereby allowing transmission of electrical output from the respective transducer to the output processing system, or disabled, thereby preventing transmission of electrical output from the respective transducer to the output processing system.

4. A method of performing sensing operations on a sample using a transducer array having a plurality of transducers, the method comprising:

attaching the sample to at least one transducer in the transducer array;

operating the transducer array sequentially through a plurality of different states, where the method includes, for each state:

activating one or more of the transducers within the transducer array, which includes applying a drive signal to the transducer and receiving a corresponding output signal for the transducer at an output processing subsystem; and isolating all non-activated transducers within the transducer array to inhibit coupling of noise contributions from the non-activated transducers to the output processing subsystem, where the transducers which are activated are varied from state to state as the transducer array is operated through the plurality of different states, thereby permitting output to be obtained for different portions of the transducer array at different times; and where the transducer array includes a local drive signal generator for each transducer of the transducer array, and where activating one or more of the transducers within the transducer array includes closing a switch between the transducer to be activated and the local drive signal generator associated with such transducer.

5. A method of performing sensing operations on a sample using a transducer array having a plurality of transducers, the method comprising:

attaching the sample to at least one transducer in the transducer array;

operating the transducer array sequentially through a plurality of different states, where the method includes, for each state:

activating one or more of the transducers within the transducer array, which includes applying a drive signal to the transducer and receiving a corresponding output signal for the transducer at an output processing subsystem; and isolating all non-activated transducers within the transducer array to inhibit coupling of noise contributions from the non-activated transducers to the output processing subsystem, where the transducers which are activated are varied from state to state as the transducer array is operated through the plurality of different states, thereby permitting output to be obtained for different portions of the transducer array at different times; and where the transducer array includes a local drive signal generator for each transducer of the transducer array, and where activating one or more of the transducers within the transducer array includes enabling the local drive signal generator associated with the transducer to be activated and closing an input switch coupled between the local drive signal generator and the transducer to be activated.

6. A transducer-based sensor system, comprising:

a transducer array implemented within a microchip, the transducer array including a plurality of transducers, where at least one transducer in the transducer array is configured to have a sample material attached thereto;

an output processing subsystem coupled with the transducer array; and a selector coupled with the transducer array and configured to selectively activate transducers within the transducer array by applying an enabling signal to the transducer array for at least one, but less than all, of the transducers, such that the transducer array includes at least one selected transducer and at least one unselected transducer, where:

for a selected transducer, application of the enabling signal enables a transmission path between the selected transducer and the output processing subsystem, thereby permitting output signals to be transmitted from the selected transducer to the output processing subsystem, where the transducer array includes a local drive signal generator for each transducer of the transducer array, and where activating one or more of the transducers within the transducer array includes closing a switch between the transducer to be activated and the local drive signal generator associated with such transducer.

7. A transducer-based sensor system, comprising:
a transducer array including a plurality of transducers;
an output processing subsystem coupled with the transducer array; and
a selector coupled with the transducer array and configured to selectively activate transducers within the transducer array by applying an enabling signal to the transducer array for at least one, but less than all, of the transducers, such that the transducer array includes at least one selected transducer and at least one unselected transducer, where:
for a selected transducer, application of the enabling signal enables a transmission path between the selected transducer and the output processing subsystem, thereby permitting output signals to be transmitted from the selected transducer to the output processing subsystem;
the transducer array is configured to isolate any unselected transducers from the output processing subsystem, where such isolation is obtained by disabling the transmission paths, thereby substantially preventing output signals from being transmitted from the unselected transducers to the output processing subsystem;
a local drive signal generator for each transducer, where the selector is configured to control transducer activation for each transducer by permitting drive signals to be applied from the local drive signal generator to each selected transducer, and by preventing drive signals from being applied from the local drive signal generator to each unselected transducer; and
a switch coupled between each transducer and each transducer's local drive signal generator, the switch being configured to close if the transducer is selected, and to open if the transducer is unselected.

8. A transducer-based sensor system, comprising:
a transducer array including a plurality of transducers, where at least one transducer in the transducer array is configured to provide both bulk wave and surface wave modes of operation;
an output processing subsystem coupled with the transducer array; and
a selector coupled with the transducer array and configured to selectively activate transducers within the transducer array by applying an enabling signal to the transducer array for at least one, but less than all, of the transducers, such that the transducer array includes at least one selected transducer and at least one unselected transducer, where:
for a selected transducer, application of the enabling signal enables a transmission path between the selected transducer and the output processing subsystem, thereby permitting output signals to be transmitted from the selected transducer to the output processing subsystem; and
the transducer array is configured to isolate any unselected transducers from the output processing subsystem, where such isolation is obtained by disabling the transmission paths, thereby substantially preventing output signals from being transmitted from the unselected transducers to the output processing subsystem.

9. A transducer-based sensor system, comprising:
a transducer array including a plurality of transducers configured to be placed into operative proximity with a sample material, and configured to produce electrical output based upon drive signals applied to the transducers and upon the sample material, where at least one transducer in the transducer array is a surface acoustic wave device;
an output transmission path associated with each transducer, each output transmission path being defined between its associated transducer and an output processing subsystem configured to receive electrical output from the transducers; and
a selector configured to control activation and deactivation of portions of the transducer array by enabling and disabling the output transmission paths such that each output transmission path is either enabled, thereby allowing transmission of electrical output from the respective transducer to the output processing system, or disabled, thereby preventing transmission of electrical output from the respective transducer to the output processing system; and
where the transducer array includes a local drive signal generator for each transducer of the transducer array, and where activating one or more of the transducers within the transducer array includes closing a switch between the transducer to be activated and the local drive signal generator associated with such transducer.

* * * * *

UNITED STATES PATENT AND TRADEMARK OFFICE
CERTIFICATE OF CORRECTION

PATENT NO. : 7,117,743 B2
APPLICATION NO. : 10/632290
DATED : October 10, 2006
INVENTOR(S) : Daniel R. Blakley It is certified that error appears in the above-identified patent and that said Letters Patent is hereby corrected as shown below:

In column 6, line 33, delete "pausing" and insert -- causing --, therefor.

In column 11, line 25, delete "within" and insert -- with the --, therefor.

In column 13, line 24, in Claim 2, after "path" delete ",".

In column 13, line 24, in Claim 2, after "for the" delete "tranducer" and insert -- transducer --, therefor.

Signed and Sealed this

Twenty-eighth Day of April, 2009

JOHN DOLL
*Acting Director of the United States Patent and Trademark Office*